United States Patent [19]

Sekikawa et al.

[11] Patent Number: 4,996,220

[45] Date of Patent: Feb. 26, 1991

[54] METHOD OF PRODUCING A CLATHRATE COMPOUND

[75] Inventors: Ayako Sekikawa; Hideo Sugi; Ryoichi Takahashi, all of Tokyo, Japan

[73] Assignee: Kurita Water Industries Ltd., Tokyo, Japan

[21] Appl. No.: 506,066

[22] Filed: Apr. 9, 1990

Related U.S. Application Data

[62] Division of Ser. No. 295,628, Jan. 10, 1989.

[30] Foreign Application Priority Data

Jan. 25, 1988 [JP] Japan .................................. 63-13800

[51] Int. Cl.$^5$ ..................... A01N 25/08; A01N 25/34; A01N 33/26; A01N 43/80
[52] U.S. Cl. .................................... 514/372; 514/664; 423/407; 548/213; 424/468; 424/469; 424/470
[58] Field of Search ................ 548/213; 514/372, 664; 423/407

[56] References Cited

U.S. PATENT DOCUMENTS 3,975,155 8/1976 Geyer .............................. 548/213 X

FOREIGN PATENT DOCUMENTS 46-21240 6/1971 Japan .
58-15577 9/1983 Japan .
61-53201 3/1986 Japan .
63-295568 12/1988 Japan .

Primary Examiner—Richard L. Raymond
Attorney, Agent, or Firm—Kanesaka and Takeuchi

[57] ABSTRACT

A clathrate compound is produced if a powdery host compound which reacts with a microbicide to form the clathrate compound is added into an aqueous solution of the microbicide. If the microbicide is separated from the clathrate compound, a microbicide of high purity can be obtained.

5 Claims, No Drawings

METHOD OF PRODUCING A CLATHRATE COMPOUND

This is a division, of application Ser. No. 295,628, filed Jan. 10, 1989 pending.

FIELD OF THE INVENTION AND RELATED ART STATEMENT

This invention relates to a method of producing a clathrate compound. More particularly, it relates to a novel method for the production of a clathrate compound which can overcome any problem arising from the use of an organic solvent.

A clathrate compound is a compound of the type which is formed by retaining guest molecules in the holes of host molecules. The clathrate compounds have been expected to be useful for a wide range of applications.

It has hitherto been usual to produce a clathrate compound by adding a solution prepared by dissolving a host compound in a solvent into a solution containing a guest compound and causing the two compounds to react with each other. This method has, however, been found to involve the following problems:

(1) The formation of a clathrate compound depends on the solvent which is employed;

(2) A clathrate compound in which no guest molecule is included, but in which the solvent is included, is sometimes produced;

(3) The problems (1) and (2) make it difficult to choose an appropriate solvent;

(4) Even if an appropriate solvent is employed, the precipitation of only the clathrate compound in which the guest molecules are included can be achieved only under limited conditions, including temperature, the ratio of the host and guest molecules which are employed, their concentrations in the solutions, and stirring of the solution, which are difficult to select;

(5) Special disposal is required for the waste solution remaining after the separation of the solid from the reaction product;

(6) It is necessary to employ facilities for protecting workers and their working environment, particularly when an organic solvent is used; and (7) It is impossible to obtain any product containing 100% of the host compound which has been employed.

The compound of formula (I) below, i.e. 5-chloro-2-methyl-4-isothiazolin-3-one (hereinafter referred to simply as "CMI"), has been widely used as a slime controller, bactericide, algicide or fungicide in cooling water systems, water systems in the paper and pulp industry, swimming pools and other water systems, owing to its high antimicrobial activity:

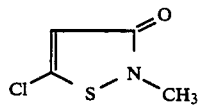

(I)

CMI is usually produced by:
(1) the halogenation of -thioketoamide in an inert organic ester solvent, such as an acetic acid ester, or
(2) the treatment of a -substituted thiocyanoacrylamide or thiosulfatoacrylamide with an acid to obtain isothiazolone and the halogenation thereof, as disclosed in Japanese Patent Publication No. 21240/1971.

Neither of these two methods (1) and (2) can, however, make a product which is composed solely of CMI. They can only make a product containing as a by-product 2-methyl-4-isothiazolin-3-one (hereinafter referred to simply as "MI") of formula (II) below having an antimicrobial activity which is as low as only one-tenth of that of CMI:

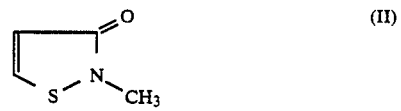

(II)

Moreover, it has hitherto been impossible to separate only CMI from the reaction product. Therefore, there has been no alternative but to use any such product containing MI having only a very low degree of antimicrobial activity.

OBJECTS AND SUMMARY OF THE INVENTION

It is an object of this invention to overcome the drawbacks of the prior art as hereinabove pointed out and provide a method which makes it possible to produce a clathrate compound easily and efficiently without using any solvent.

It is another object of this invention to provide a method which makes it possible to separate only the desired microbicide easily and efficiently from a mixed solution containing it and thereby produce a microbicide of high purity.

The method of this invention for producing a clathrate compound is essentially characterized by adding into an aqueous solution of a microbicide a powdery host compound which reacts with the microbicide to form a clathrate compound.

The method of this invention for purifying a microbicide is essentially characterized by adding into an aqueous solution of a microbicide a powdery host compound which reacts with the microbicide to form a clathrate compound, and separating the microbicide from the clathrate compound.

We, the inventors of this invention, have made an extensive study of the possibility of overcoming the drawbacks of the prior art which occur due to the solvent used. As a result, we have discovered that the direct addition of a powdery host compound into a solution containing a guest compound makes it possible to form a clathrate compound very efficiently, and that the efficient separation and purification of any desired microbicide is possible by the selective formation of its clathrate compound. This discovery forms the basis of our invention.

DETAILED DESCRIPTION OF PREFERRED EMBODIMENTS

Referring now in detail to this invention, it is possible to use any microbicide as a guest compound without any particular limitation if it can form a clathrate compound with an appropriate host compound. Two examples of the guest compounds which can be employed are CMI of formula (I) and hydrazine:

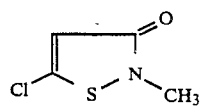

They both are widely used as an effective water-soluble microbicide.

There is no particular limitation to the powdery host compound which can be employed for the purpose of this invention. It is possible to use any compound that can form a clathrate compound by including the microbicide as the guest compound. Eight compounds will, therefore, be shown below merely by way of example:

(1) 1,1,6,6-tetraphenyl-2,4-hexadiyne-1,6-diol (hereinafter referred to simply as "TPH")

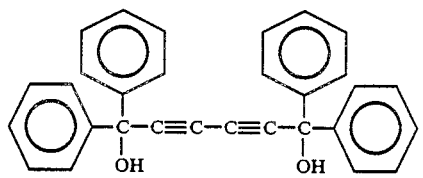

(2) 1,1-di(2,4-dimethylphenyl)-2-propyne-1-ol (hereinafter referred to simply as "DMP")

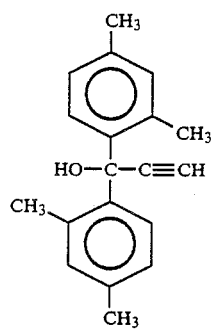

(3) 1,1,4,4-tetraphenyl-2-butyne-1,4-diol (which will sometimes be referred to simply as "TPB")

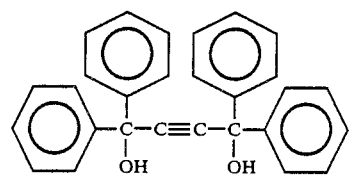

(4) 9,10-di(4-methylphenyl)-9,10-dihydroanthracene-9,10-diol (which will sometimes be referred to simply as "PhHA")

(5) 1,1-bis(4-hydroxyphenyl)-cyclohexane (which will sometimes be referred to simply as "PhCH")

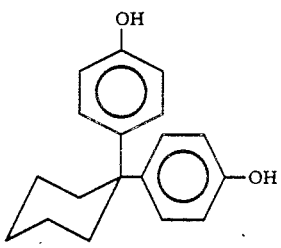

(6) 1,1,6,6-tetra(2,4-dimethylphenyl)-2,4-hexadiyne-1,6-diol (which will sometimes be referred to simply as "TDPh")

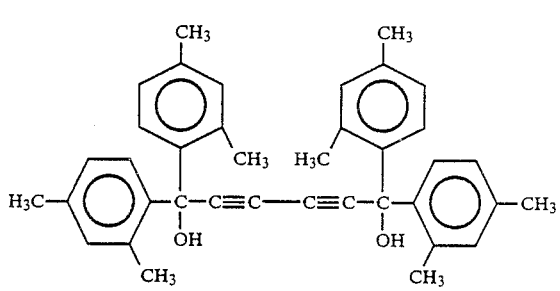

(7) 1,1'-bi-2-naphthol (which will sometimes be referred to simply as "β-dinaphthol")

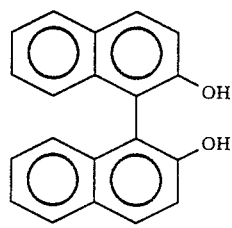

(8) Diphenic acid bis(dicyclohexylamide) (which will sometimes be referred to simply as "DPhHA")

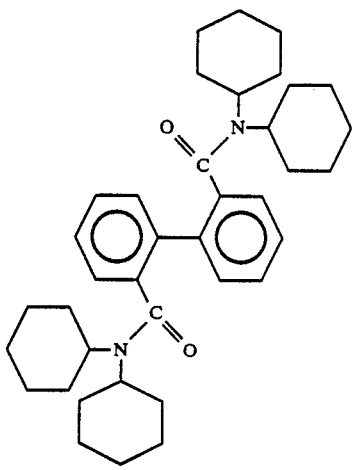

According to the method of this invention for producing a clathrate compound, powder of a host compound is added directly to an aqueous solution of a microbicide as the guest compound which can form a clathrate compound with the host compound, and is mixed therein, while the solution is stirred. The aqueous solution does not necessarily need to be one containing only the microbicide, but may contain impurities, too. Even if it may contain any byproduct or other impurities, the method of this invention enables the host compound to react with the microbicide so selectively that the resulting clathrate compound is composed solely of the host compound and the desired microbicide.

Although there is no particular limitation to the concentration of the microbicide in its solution which can be employed, it is in the range of usually from 1 to 99% by weight and preferably from 5 to 99% by weight. The reaction between the host compound and the microbicide is continued for a period of time ranging usually from about five minutes to five hours and preferably from about 0.5 to about four hours. The amounts of the host compound and the microbicide which are employed may be, say, from one to three times as large as their chemical equivalents.

The reaction may be caused to take place at any temperature in the range of 0° C. to 100° C. A preferred temperature range is, however, from 25° C. to 95° C., and a more preferable range from 50° C. to 95° C. The higher the temperature, the shorter the reaction time will be.

When a reaction temperature exceeding a certain level is employed, it is sometimes likely that the reaction product may be partly oily and be separated into an aqueous and an oily layer. The oily layer contains a clathrate compound. The reaction product obtained in a temperature range in which no such oily matter is formed is in the state of a suspension in which no clathrate compound is dissolved. However, the formation of oily matter does not always occur, but there are some combinations of host and guest compounds not forming any oily matter at any temperature below 100° C., i.e. the boiling point of water.

The clathrate compound which has been formed can be separated from the reaction product:

(1) by a suction filter if the reaction product is in the state of a suspension; or (2) if the reaction product contains an oily layer, the oily layer is separated therefrom and cooled to room temperature, whereby a solid clathrate compound is obtained, or the reaction product is left at a standstill and cooled to room temperature to allow the oily matter to solidify and the solidified matter is separated from the reaction product. In either event, the clathrate compound is easy to separate from the reaction product.

The clathrate compounds according to the method of this invention are usually produced as a result of the reactions represented by the following equations, the right side of each equation showing the clathrate compound obtained as a result of the corresponding reaction:

TPH+2CMI→TPH·(CMI)$_2$

2DMP+CMI→(DMP)$_2$·CMI

TPH+2N$_2$H$_4$·H$_2$O→TPH·(N$_2$H$_4$·H$_2$O)$_2$

TPB+2CMI→TPB·(CMI)$_2$

PhHA+2CMI→PhHA·(CMI)$_2$

PhCH+CMI→PhCH·CMI

TDPh+CMI→TDPh·CMI

β-dinaphthol+CMI→β-dinaphthol·CMI

3DPhHA+CMI→(DPhHA)$_3$·CMI

Every clathrate compound that is produced by the method of this invention is usually a powdery solid and is, therefore, easy to form into tablets or any other shape. Insofar as the microbicide is employed as the guest compound, the clathrate compound according to the method of this invention is low in toxicity and is, therefore, easy to handle. Moreover, it is an effective sustained release antimicrobial agent which can maintain its antimicrobial activity for a long period of time, as it releases the microbicide in a sustained way in water.

According to the method of this invention for purifying a microbicide, only the microbicide is separated from the clathrate compound which has been produced by adding the powdery host compound into the aqueous solution of the microbicide containing impurities, as hereinabove described.

Although it has hitherto been difficult to obtain CMI selectively as hereinbefore stated, the method of this invention makes it possible to obtain a highly purified product of CMI by separating CMI from the clathrate compound in which only CMI is included in the host compound, and which can be produced only if the powdery host compound is added directly into, for example, an aqueous solution of a mixture of CMI and MI.

The microbicide, such as CMI, can be separated from the clathrate compound by:

(1) dipping the clathrate compound in water; or (2) dissolving the clathrate compound in an organic solvent and adding water to its solution to cause only the host compound to settle. In either event, the microbicide is dissolved in water and can be recovered in the form of its aqueous solution.

The method of this invention for producing a clathrate compound has a number of advantages including:

(1) eliminating any difficulty in the selection of the solvent;

(2) simplifying the reaction and the selection of its conditions;

(3) enabling the use of the residual reaction product as a diluent for the aqueous solution of the microbicide; and (4) enabling the recovery of virtually 100% of the host compound, thereby making it possible to produce a clathrate compound which is useful as a sustained release antimicrobial agent, or the like, easily at a low cost with a high degree of selectivity and a high yield.

The method of this invention for purifying a microbicide makes it possible to obtain a microbicide of high purity by separating selectively and efficiently the microbicide, such as CMI, which has hitherto been difficult to separate.

The invention will now be described more specifically with reference to several examples thereof. It is, however, to be understood that the following description is not intended to limit the scope of this invention, but that variations or modifications may be easily made by anybody of ordinary skill in the art without departing from the scope of this invention which is defined by the appended claims.

EXAMPLE 1

Twenty grams (0.048 mole) of TPH were mixed with 15 g (0.1 mole) of an aqueous solution of KATHON 886, i.e. a mixed solution of CMI and MI produced by Rohm & Haas, which was used in its undiluted state. The mixture was caused to undergo reaction at a temperature of 70° C. for three hours under stirring, whereby a suspension was obtained. The suspension was subjected to filtration by a suction funnel, whereby a powder was collected in the funnel. Five milliliters of distilled water were added to the powder and the water containing the powder was subjected to filtration by a suction funnel, whereby the unreacted matter was washed away and removed from the powder. The powder was collected in a 200-mesh sieve and was dried by purging with dry air.

The infrared (IR) spectrum of the powder coincided with that of a clathrate compound which had been produced by employing a solvent. The NMR analysis of the powder revealed that it contained TPH and CMI in a molar ratio of 1:2 and in a weight ratio of 58:42, and did not contain any MI.

Clathrate compounds were produced by repeating Example 1 substantially, but employing the host compounds, the amounts of the aqueous solution of KATHON 886, the proportions of the host and guest compounds, and the reaction temperature and time which are shown in Table 1 below.

The IR spectrum of each clathrate compound obtained in powder form was similar to that of a clathrate compound which had been produced by employing a particular solvent. The NMR analysis of each clathrate compound revealed the molar ratio (H:G) of the host and guest compounds as shown in Table 1.

TABLE 1

| | Example | | | | | | |
|---|---|---|---|---|---|---|---|
| | 2 | 3 | 4 | 5 | 6 | 7 | 8 |
| | Host Compound | | | | | | |
| | DMP | TPB | β-dinaphthol | TDPh | PhHA | PhCH | DPhHA |
| Host Compound Amount | | | | | | | |
| (q) | 20 | 20 | 20 | 20 | 20 | 20 | 20 |
| (mol) | 0.075 | 0.051 | 0.069 | 0.038 | 0.051 | 0.075 | 0.035 |
| Guest Compound Amount | | | | | | | |
| (q) | 60 | 60 | 110 | 60 | 150 | 110 | 25 |
| (mol) | 0.042 | 0.11 | 0.076 | 0.042 | 0.104 | 0.076 | 0.017 |
| Temperature (°C.) | 25 | 70 | 25 | 90 | 70 | 25 | 70 |
| Time (hr) | 1 | 3 | 3 | 2 | 3 | 3 | 3 |
| Molar Ratio H:G | 2:1 | 1:2 | 1:1 | 1:1 | 1:2 | 1:1 | 3:1 |

EXAMPLE 9

A mixture of 20 g of DMP and 60 g of an undiluted solution of KATHON 886 was heated to 90° C. under stirring. When its temperature had reached 90° C., its stirring was discontinued and it was left at a standstill. When oily drops had begun to float, its heating was discontinued and the mixture was cooled to room temperature, whereby the oily matter was solidified to yield a solid powder.

The IR spectrum of the powder which had been collected coincided with that of a clathrate compound which had been produced by employing a solvent. The NMR analysis of the powder revealed that it contained DMP and CMI in a molar ratio of 2:1 and in a weight ratio of 78:22, and did not contain any MI.

EXAMPLE 10

A powdery clathrate compound was produced by repeating Example 9, except that 20 g of PhCH were employed as the host compound and mixed with 110 g of an undiluted solution of KATHON 886.

The IR spectrum of the powder coincided with that of a clathrate compound which had been produced by employing a solvent. The NMR analysis of the powder revealed that it contained PhCH and CMI in a molar ratio of 1:1 and in a weight ratio of 64:36, and did not contain any MI.

EXAMPLE 11

One gram of PhCH was mixed with 5 g of 80% hydrazine hydrate and after the mixture had been stirred, it was left at a standstill overnight. Then, solid matter was collected by filtration, washed carefully, and dried to yield a powder. The IR spectrum of the powder coincided with that of a clathrate compound which had been produced by employing a solvent, and confirmed that it was a clathrate compound. The NMR analysis of the powder revealed that it contained PhCH and hydrazine in a molar ratio of 1:2.

EXAMPLE 12

Each of the clathrate compounds which had been obtained in Examples 1 and 10 was placed in a 0.8μ membrane filter bag in an amount containing 0.1 g of CMI. Each bag was immersed in pure water and the water was stirred to cause the dissolution of CMI from the clathrate compound. The concentration of CMI in the water in each bag was determined when 72 hours had passed. The results of the determination showed that all of the CMI in the clathrate compound in each bag had been dissolved in the water, and that the method of this invention made it possible to recover CMI of high purity easily.

EXAMPLE 13

One gram of the clathrate compound which had been obtained in Example 10 was dissolved in 1 ml of methanol. After 1 ml of pure water had been added to the solution, it was carefully stirred. Then, the solution was subjected to filtration by a 0.45μ membrane suction filter, whereby a microbicide solution was obtained.

What is claimed is:

1. A method of producing a clathrate compound, comprising:
   preparing an aqueous solution containing a microbicide,
   preparing a host compound in the form of a powder, said host compound, when reacted with said microbicide, forming a clathrate compound together with said microbicide,
   adding said powdery host compound into the solution containing the microbicide to react the powdery host compound with the microbicide so that the clathrate compound formed of the host compound and the microbicide is formed, and
   separating the formed clathrate compound from the solution.

2. A method as set forth in claim 1, wherein said microbicide is 5-chloro-2-methyl-4-isothiazoline-3-one.

3. A method as set forth in claim 1, wherein said host compound is at least one of the following compounds:
   (1) 1,1,6,6-tetraphenyl-2,4-hexadiyne-1,6-diol;
   (2) 1,1-di(2,4-dimethylphenyl)-2-propyne-1-ol;
   (3) 1,1,4,4-tetraphenyl-2-butyne-1,4-diol;
   (4) 9,10-di(4-methylphenyl)-9,10-dihydroanthracene-9,10-diol;
   (5) 1,1-bis(4-hydroxyphenyl)-cyclohexane;
   (6) 1,1,6,6-tetra(2,4-dimethylphenyl)-2,4-hexadiyne-1,6-diol;
   (7) 1,1'-bi-2-naphthol; and
   (8) diphenic acid bis(dicyclohexylamide).

4. A method of producing a clathrate compound, comprising,
   preparing an aqueous solution containing 5-chloro-2-methyl-4-isothiazoline-3-one,
   adding at least one powdery compound which forms a clathrate compound together with 5-chloro-2-methyl-4-isothiazoline-3-one to the aqueous solution containing 5-chloro-2-methyl-4-isothiazoline-3-one to thereby form a clathrate compound, said powdery compound being selected from the group consisting of the following compounds:
   1,1,6,6-tetraphenyl-2,4-hexadiyne-1,6-diol;
   1,1-di(2,4-dimethylphenyl)-2-propyne-1-ol;
   1,1,4,4-tetraphenyl-2-butyne-1,4-diol;
   9,10-di(4-methylphenyl)-9,10-dihydroanthracene-9,10-diol;
   1,1-bis(4-hydroxyphenyl)-cyclohexane;
   1,1,6,6-tetra(2,4-dimethylphenyl)-2,4-hexadiyne-1,6-diol;
   1,1'-bi-2-naphthol; and
   diphenic acid bis(dicyclohexylamide), and
   separating the clathrate compound from the aqueous solution.

5. A method according to claim 4, wherein said aqueous solution further contains 2-methyl-4-isothiazoline-3-one.

* * * * *